United States Patent [19]

Christensen et al.

[11] Patent Number: 5,552,288
[45] Date of Patent: Sep. 3, 1996

[54] CHROMOGEN AGAR COLOR REACTIVE TEST SHEET

[76] Inventors: Dale A. Christensen; Peter Nash, both of c/o Camas Diagnostic Company, 1313 Fifth St. SE., Minneapolis, Minn. 55414

[21] Appl. No.: 402,464

[22] Filed: Mar. 10, 1995

Related U.S. Application Data

[60] Continuation-in-part of Ser. No. 957,686, Oct. 7, 1992, which is a division of Ser. No. 555,232, Jul. 20, 1990, Pat. No. 5,156,948.

[51] Int. Cl.$^6$ ................................................ G01N 33/535
[52] U.S. Cl. .............................. 435/7.9; 422/57; 435/33; 435/34; 435/39; 435/40; 435/5; 435/7.92; 435/287.2; 436/514; 436/515; 436/528; 436/529; 436/805; 436/809; 436/823
[58] Field of Search .................... 422/57, 58; 435/33, 435/34, 39, 40, 288, 291, 299, 300, 301, 5, 7.9, 7.92, 287.2; 436/514, 515, 528, 529, 805, 809, 823

[56] References Cited

U.S. PATENT DOCUMENTS 3,551,295  12/1970  Dyer ............................................. 435/34
3,814,670   6/1974  Freake et al. ............................... 435/40
3,979,263   9/1976  Bucalo ......................................... 435/34

Primary Examiner—James C. Housel
Assistant Examiner—Christopher L. Chin
Attorney, Agent, or Firm—Burd, Bartz & Gutenkauf

[57] ABSTRACT

A moist unitary non-laminar chromogen agar color reactive test sheet for use in a simplified enzyme-linked immunosorbent assay (ELISA) for the diagnosis of viral, fungal, bacterial and parasitic diseases. The diagnostic test is designed for use in non-laboratory settings where the usual equipment and supplies, including running water, may not be available. The test sheet comprises chromogen agar paper (CAP) impregnated with an enzyme substrate, and electron acceptor, if needed, in agar. It is applied over a conjugate in the form of a species specific enzyme-linked anti-immunoglobulin bound to an antibody-antigen coating of a previously prepared test plate. After incubation to cause a color reaction, the results are read and interpreted in comparison with known standards.

4 Claims, 1 Drawing Sheet

CHROMOGEN AGAR COLOR REACTIVE TEST SHEET

This application is a continuation-in-part of application Ser. No. 957,686 filed Oct. 7, 1992, which in turn is a division of application Ser. No. 555,232 filed Jul. 20, 1990. now U.S. Pat. No. 5,156,948 issued Oct. 20, 1992.

BACKGROUND OF THE INVENTION

1. Field of the Invention

Many viral, fungal, bacterial and parasitic diseases are detrimental to human and animal welfare. Convenient, economic and meaningful test procedures are needed to assist the medical and veterinary communities to diagnose and combat these diseases.

This invention relates to a diagnostic method and test kit which have the advantage of being simple to use, economical, rapid and require no special equipment. Since no instruments are required, the test can be run by veterinarians on a farm, by medical and veterinarian personnel in an office setting or in other settings where instruments, running water and other laboratory equipment and supplies are not available.

2. The Prior Art

Many techniques are available to test for microbial diseases. The test of the present invention falls into the category of antibody detection as do many other existing tests. Among these are immunodiffusion, serum neutralization, immunofluorescent staining and the enzyme-linked immunosorbent assay (ELISA) technique developed by Envall and Perlmann in 1972. The samples for these tests are usually blood, plasma, serum or other body fluids or tissues.

All of the tests involve the binding of antibodies in the sample with controlled amounts of antigen. The antigen may either be added in liquid form, as is done with immunodiffusion plates, or immobilized on a surface as part of the test system, as is done with the popular 96-well ELISA technique. Detection of antibody is done by viewing a precipitation line in immunodiffusion techniques, by observing fluorescence in staining techniques, and by observing color generation in enzymatic techniques.

The ELISA multi-well techniques have the following procedural similarities:

1. Wells of polystyrene micro-titer plates are sensitized by passive absorption with the relevant antigen; the plates are then washed.
2. The test samples are incubated in the sensitized well and the plates are again washed. Antibody present in that sample reacts with and is bound to the immobilized antigen on the well surfaces.
3. Enzyme-labeled anti-Ig (i.e., of an immunoglobulin animal species corresponding to the sample) conjugate is incubated in the wells. The conjugate contains an enzyme such as peroxidase, glucose oxidase, beta-galactosidase or alkaline phosphatase. The conjugate reacts with any "captured" or bound antibody. Excess reagent is washed away.
4. Enzyme substrate is added and the plates are incubated; the rate of degradation is indicated by a color change, which is proportional to the antibody concentration in the test samples in Step 2.
5. The reaction is stopped or allowed to arrest and the color change is assessed visually or in a spectrophotometer.

The use of an ELISA-type antibody detection technique to diagnose pseudorabies in swine is exemplified by Joo U.S. Pat. No. 4,562,147.

The basic technique of the ELISA test has been modified by the method of the present invention to significantly reduce the steps needed to conduct the test and to enable the user to read results without the need of instrumentation.

SUMMARY OF THE INVENTION

Broadly stated, the diagnostic method of the present invention comprises the following steps: Purified viral, fungal, bacterial or parasitic antigen is collected in the presence of a detergent. An optimal concentration of the solubilized antigen diluted in a coating buffer is adsorbed on a supporting surface. After antigen coating, the surface may be further treated by an incubation with a blocking agent. A thin layer of agar is applied to the surface and allowed to solidify. The resulting test tray is prepared in advance of need and represents a part of a diagnostic kit for the detection of antibodies to microbial infections.

Sections of absorbent or penetrable material, such as paper are cut to shape to just fit into the section of the surface of the test trays which were treated with antigen. An amount of liquid agar containing a suitable concentration of enzyme substrate and acceptor, if needed, is applied to the paper in an evenly distributed fashion and allowed to solidify. The resulting absorbent material is prepared in advance of need and stored in a protective environment.

On location of testing, samples, such as blood or serum, are collected in liquid form or applied to an absorbent paper and are placed on identifiable positions on the surface of the agar of the previously prepared test tray and allowed to incubate to bind antibodies from the blood or serum samples to the antigen coating of the test tray. The agar is removed and the surface is washed. A conjugate solution is applied to the test tray. After incubation to bind the conjugate to the antibodies, the excess conjugate solution is removed and the surface is washed. The previously prepared chromogen test paper (CAP) is applied in intimate contact with the bound conjugate. Positive results are indicated by a color reaction between the bound antigen-antibody-conjugate on the surface of the test tray and the CAP. The tray is inverted and the developed color reaction zones are visually interpreted.

The invention includes a diagnostic kit for field testing.

BRIEF DESCRIPTION OF THE DRAWINGS

The invention is illustrated by the accompanying drawings in which corresponding parts are identified by the same numerals and in which.

DETAILED DESCRIPTION OF THE PREFERRED EMBODIMENT

A. Preparation of Test Plates

Figure 1:
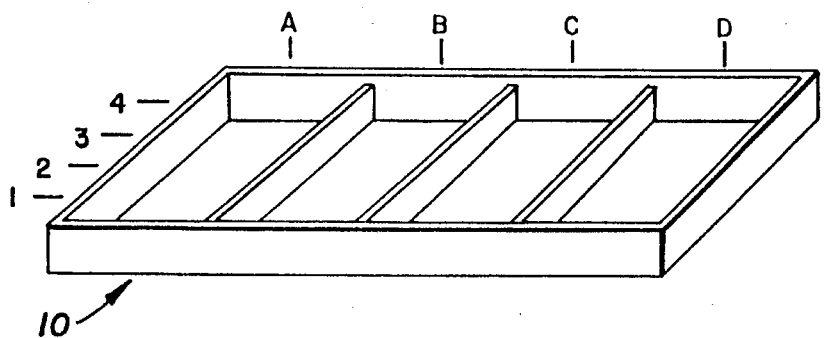
FIG. 1 is a perspective view of one form of tissue culture tray which may be used in carrying out the method of this invention, shown without its cover.

Referring now to the drawings, there is shown one form of test plate which may be used in carrying out the diagnostic test method of the present invention. This exemplary four chambered tissue culture tray, indicated generally at 10, is available commercially from Nunc, Incorporated. Desirably the tray is divided into a plurality of identifiable zones. For example, the tray may be marked on the bottom side to indicate 16 zones. This can be accomplished by labeling the four chambers "A", "B", "C" and "D" and, at approximately equal distances vertically, labeling the numbers "1", "2", "3" and "4" on the tray. The 16 zones are thus denoted as A-1, A-2, etc. to D-4. The tray chambers may be cleaned, as by adding an agent such as ethanol, methanol, isopropanol, and the like, to each chamber and incubating for about 10 to 20 minutes at room temperature. Alternatively, petri dishes, multi-well microtitration plates, and the like, may be used.

A source of viral, fungal, bacterial or parasitic antigen, such as pseudorabies virus is added in dilute solution of concentrations of about 5 to 100 μg protein or lipopolysaccharide per milliliter to each chamber of tray 10 and incubated for sufficient time to cause the antigen to become attached to the tray surface. Many antigens may be incubated for about 2 to 4 hours at room temperature. Other antigens preferentially bind at different conditions, such as 3 hours at 37° C. followed by overnight at 4° C.

Figure 2:
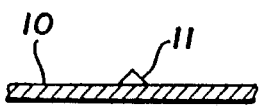
FIG. 2 is a sectional view, on a greatly enlarged scale, showing schematically the presence of antigen adhering to the bottom surface of a well in the tissue culture tray.
Figure 3:
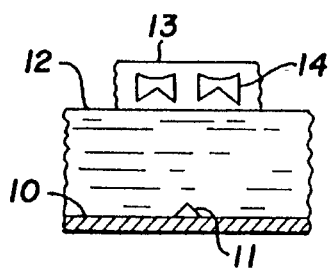
FIG. 3 is a similar sectional view showing a layer of agar applied on the antigen and a paper sample disk containing antibody resting on the agar.

After binding of the antigen, the excess solution is then discarded and the tray compartments, now bearing attached antigen 11 (FIG. 2) are refilled with a solution of a blocking agent, such as albumin, non-fat milk, ovalbumin, gelatin, serum, and the like, for the purpose of attaching an inert material to plastic binding sites which were left exposed after the incubation with antigens. This step reduces the non-specific adsorption of antibody molecules which are not directed at the specific antigen and reduces non-specific adsorption of the conjugate which is important in the color generating steps. The solution is incubated for another 10 to 60 minutes and discarded. A thin layer of a 0.8 to 2% solution of a suitable agar or gel, such as Type E agar (available commercially from Sigma Chemical Company) maintained within 7° of 90° C. is added. Tray covers are added. The agar 12 (FIG. 3) is allowed to cool and set at room temperature. The trays are enclosed in plastic or foil bags and then stored refrigerated until needed.

Methods are known to isolate antigens from virus particles. An antigen, however, that can be obtained from a suspension of purified virus will be almost free from contaminating host material. This is likely to provide an antigen free of other antigens. The growth of virus is frequently achieved in tissue culture, in chorioallantoic membranes or in organ tissue such as rabbit skin. Following prescribed purification protocols, the antigens from virus particles are dissolved and stored in a frozen state. In some instances, the desired product is a soluble antigen or a nucleoprotein antigen rather than the virus particle.

The preparative methods for bacterial antigens are quite varied. Because of considerable dissimilarity of components of different bacterial species, methods of wide application are few. Bacterial antigens may be: 1) extracellular such as extracellular proteins, flagella and exopolysaccharides; 2) part of the cell wall; 3) part of the cell membrane; or 4) intracellular components.

Some parasitic antigens may be derived from animal blood infected with the particular organism. The blood may be cultured (as with *P. falciparium* or *B. divergens*) and parasitized erythrocytes are collected by centrifugation, washed and stored. In some cases (as with *T. brucei*) packed trypanosomes are collected free of erythrocytes. In other cases, ion exchange columns are used to purify the parasite from the infected blood. Some parasitic antigens (as with *T. gondii*) may be derived from the ascitic fluid of infected mice. Some larger parasites (as *O. gutturosa*) may be obtained by isolating adult worms from infected animals and homogenizing them. The packed parasitic organisms obtained from any of the above sources may be suspended in buffer, subjected to one or more freeze-thaw cycles and sonically disrupted, The material may then be centrifuged (e.g. 30 minutes at 10,000 rpm) to sediment the debris. Supernatant material may be frozen and stored for future use as stock antigen.

Antigens may be purchased from such companies as Immuno-Mycologics, Inc., Biodesign International and Cambridge Medical Technology Corporation. Lipopolysaccharides, which are cell wall components, may be purchased from Sigma Chemical Company.

B. Preparation of Chromogen Agar Paper (CAP)

Figure 7:
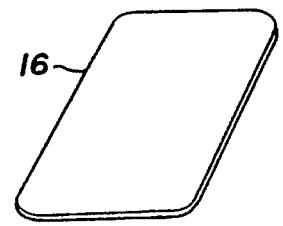
FIG. 7 is a perspective view of one form of CAP.
Figure 8:
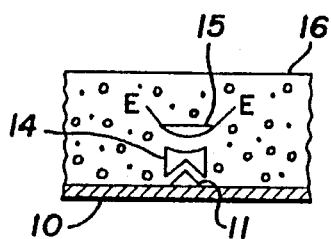
FIG. 8 is a sectional view, like FIG. 6, showing the addition of a CAP to the reaction product thereof.

A white absorbent paper, such as No. 410 filter paper available commercially from Schleicher & Schuell, Inc., is impregnated with a solution of agar containing, as a chromogen, a color reactive substrate for the enzyme of a conjugate, which is in the form of a species specific enzyme-linked anti-immunoglobulin, and co-factors, and the agar is allowed to solidify. The paper may be impregnated and then cut into smaller rectangular patches corresponding in size and shape to compartments of the test tray or, preferably, the paper is first cut into rectangles and then impregnated. For example, when the enzyme is a peroxidase, the paper rectangles may be positioned on a smooth flat surface and to each is added 1.8 ml of a solution of 1.6% Type E agar in 0.01 M phosphate buffered saline (PBS) maintained within 5° of 75° C., and containing 100 microliters of 3% hydrogen peroxide ($H_2O_2$) as an electron acceptor and 4 ml of 0.32% 3,3',5,5'-tetra-methylbenzidine as an enzyme substrate, per 50 ml of agar. The agar is allowed to solidify and the resulting moist uniform non-laminar CAPs 16 (FIGS. 7 and 8) to retain their moisture are then transferred to a foil or plastic pouch container which will allow minimal exposure to heat and air circulation. The packaged CAPs are placed in a refrigerated environment until needed. For convenience, the assay may be referred to as the acronym AD-CAP-ELISA (Agar Diffusion-Chromogen Agar Paper—Enzyme-linked Immunosorbent Assay).

C. Preparation of Sample

A blood or blood serum sample containing antibodies may be applied directly to the surface of the agar layer 12 of the test tray. Preferably, however, blood or serum is dropped onto an absorbent paper (e.g. No. 903 filter paper available commercially from Schleicher & Schuell, Inc.). A drop of blood from the animal's ear or tail is applied to the paper. Alternatively, blood or serum from collection tubes may be added to the paper. The sample is allowed to dry. This allows the sample to be conveniently identified, transported and stored until needed. A 0.25 inch diameter disk 13 (FIGS. 3 and 4) is punched from the sample treated paper and applied to the test plate.

D. Application of Sample

The sample disks 13 for a 16 sample per tray layout may be initially placed on an organizing template. This a lows the disks to be recorded on a record sheet in a systematic way (e.g. A-1, A-2, etc., to D-4). Using tweezers, the disks 13 are placed on the designated positions on the surface of the agar 12. The disks are tapped gently so that they rest evenly on the agar surface and so that they also are consistently moistened from the agar. The tray cover is replaced and the samples are incubated for about two hours at room temperature.

Figure 4:
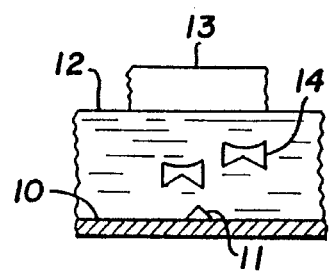
FIG. 4 is a similar sectional view showing antibodies diffused from the sample disk into the agar layer.
Figure 5:
FIG. 5 is a similar sectional view showing a portion of the antibodies bound to the antigen, the agar layer having been removed.

During this incubation period, antibodies 14 in the sample diffuse through the agar as shown in FIG. 4. Some antibodies migrate to the surface adsorbed antigen 11 and become immunologically bound as shown in FIG. 5.

E. Removal of Sample and Wash

Following the sample incubation, the agar 12 may be easily removed by lifting one end with a spatula and inverting the tray.

The entire slab of agar, along with the sample disks 13, falls out easily and cleanly. Some 3 ml of 0.1M Tris buffer, pH 7.0, containing 1% ovalbumin and 0.5% Tween 20 (Wash Solution Number One) are added to each chamber of the tray. Alternatively, PBS, BBS, or other buffers containing protein and a detergent may be used. After a brief incubation period (e.g. one to three minutes) the wash solution is discarded. Next, 3 ml of 0.1M carbonate-bicarbonate buffer, pH 9.5 (Wash Solution Number Two) is added to each chamber. Following a similarly brief incubation, the second wash is discarded.

F. Incubation with Conjugate

Figure 6:
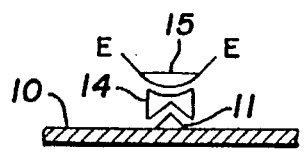
FIG. 6 is a similar sectional view showing an enzyme-IgG-conjugate bound to the sample antibody.

A conjugate in the form of a species-specific enzyme linked anti-immunoglobulin is applied to the test plate. For diagnosis of pseudorabies in swine, the conjugate is an anti-swine immunoglobulin having an enzyme chemically bound (conjugated) to it. Horseradish peroxidase coupled to the IgG fraction of anti-pig IgG 15 (FIG. 6) can be obtained commercially (Sigma Chemical Company). A dilution, determined from previous optimization studies is chosen such that a suitable color development is obtained under the conditions of the test. A typical dilution of 1:20,000 is made in Tris-Tween buffer. Alternatively, phosphate buffered saline with bovine serum albumin, a buffer such as Tween 20 in phosphate buffered saline, or even water, may be used as the diluent. Some 2 ml of the diluted conjugate solution is added to each chamber of the tray and incubated for about one hour at room temperature. As seen schematically in FIG. 6, the conjugate 15, immunoglobulin with bound enzyme E, binds to the antibodies adhering to the antigen layer 11.

The enzyme can be any one of a number which react with a substrate to produce a colored component. For example, peroxidase such as that obtained from horseradish, produces a purple color when reacted with aminosalicylic acid and hydrogen peroxide, or p-phenylene diamine and hydrogen peroxide, or tetra-methyl benzidine and hydrogen peroxide. Other materials, like uric oxide, may be used to replace hydrogen peroxide as the acceptor. Alkaline phosphatase produces a yellow color when reacted with dinitrophenylphosphate. Beta galactosidase reacts with O-nitrophenyl-beta-D-galactophyranoside to give a purple color.

Conjugates are commercially available. Most are made in the goat or rabbit. Peroxidase conjugated rabbit anti-swine immunoglobulins may be obtained from Jackson Immunological Co. or Sigma Chemical, Company and others.

G. Wash and Application of the CAP

Following the incubation, the conjugate solution is discarded and the overturned tray is tapped on a blotter to drain out most of the residual solution. Some 3 ml of Wash Solution Number One is added, the tray is tilted back and forth four or five times and allowed to stand about another minute. Wash Solution Number One is discarded and the process is repeated with Wash Solution Number Two.

Figure 9:
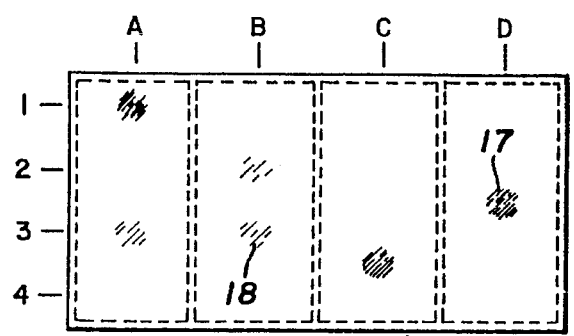
FIG. 9 is a plan view of the inverted culture tray after completion of the diagnostic test showing strongly positive, weakly positive and negative color reactive zones.

CAPs are applied to each test site by gently raising one end of a CAP from its storage container with a smooth object, such as a spatula, and picking it up by the edges. Each CAP is placed gently and smoothed flat against the surface of the test tray with no entrapped air gaps. The tray 10 is inverted and left upside down as shown in FIG. 9. The results are read after about 15 minutes.

H. Interpretation of Results

Reference samples, prepared from pools of serum having known serum neutralization (SN) values of 1:16 or 1:4 or zero are made in advance. A reference scale of color may be chosen, an example of which is: SN 1:16=5, SN 1:4=3 and SN zero=0. Pseudorabies virus negative samples have color estimated to be 0 to 1. Since individual color judgment varies, evaluations will vary to some degree. Individual users may run several known negative samples to establish their criteria for weak-color negatives. Example results are shown in FIG. 9 with a strong positive 17 at test sites A-1, C-4 and D-3; a weak, border-line positive 18 at A-3, B-2 and B-3; along with negative color development at the remaining test sites.

As seen from the aforesaid description, the basic technique of the ELISA test as exemplified by U.S. Pat. No. 4,562,147 has been modified and simplified by the test of the present invention to significantly reduce the steps needed to conduct the test and to enable the user to read results without the need of instrumentation. Agar or gel allows for a bank of potential wells to pre-exist in the body of the agar. After the antibody has been captured, the agar (with the well barriers) is removed. Subsequent washes and the addition of conjugate can now be completed with one large pipetting step which applies to the entire unbounded area.

Example: After addition of the sample, the present test requires from one-eighth to one-fourth as many maneuvers for each of the two wash steps and a similar reduction for the addition of the conjugate. In addition, the present test requires from six to twelve fold fewer maneuvers for the addition of the chromogenic substrate.

The present test has further advantages in reducing the time and effort involved in adding the enzyme substrate. No mixing of reagents nor pipetting of reagents is required for this color development part of the test. The proper amounts of critical reagents are already present in the CAP which is simply transferred to the tray chamber. Having adhesive properties, the CAP stays intact when the tray is turned upside down for viewing. The CAP is white in color, thus providing an excellent background for observing colored areas on the tray surface.

For ease of administration of the diagnostic test in the field, the materials are preferably assembled in a kit. Such a kit includes previously prepared test plates or trays; previously prepared CAPs; absorbent test sample paper, preferably partially prepunched; conjugate solution; Wash Solutions Number One and Two; and instructions for use including table or chart for interpretation of the results. Positive and negative control serum may optionally be included.

The size and quantity of the components depends upon the size of the group to be tested. A typical kit for testing 16 samples may include a transparent four chamber polystyrene Nunc tissue culture tray having the identifiable test sites; four CAPs pre-cut to fit the tray chambers, a piece of absorbent paper pre-punched to provide at least 16 circular 0.25 inch sample disks; a vial of about 10 ml dilute conjugate solution; vials of about 15 mls each of Wash Solutions Number One and Two and a disposable pipette.

Other antigens which may be used to coat surfaces include antigenic polysaccharides such as those listed in U.S. Pat. No. 4,275 149 column 14, lines 30–63. Viruses, bacteria, parasites, fungi and other microorganisms may be used intact, lysed or fragmented and the resulting composition, or a fractionated or extracted portion, may be used to coat an appropriate surface. Examples of Such microorganisms are tabulated in U.S. Pat. No. 4,275,149, columns 15–16, lines 1–69 and column 17, lines 1–22. Such lists may be expanded to include antibody detection for microorganisms of interest in the veterinary field. Extensive examples of microbial diseases in birds and animals are referred to in "1984 Yearbook of Agriculture: Animal Health, Livestock and Pets", U.S. Government Printing Office: 1984-451-784. Some examples by way of illustration are given in the following table:

| MICROORGANISM | HOST |
| --- | --- |
| Viruses: | |
| Feline Panleukopenia Virus | Cats |
| Avian Influenza Virus | Birds |
| Pseudorabies Virus | Swine |
| Bovine Viral Diarrhea | Cattle |
| Cytomegalovirus | Man |
| Transmissible Gastroenteritis Virus | Swine |
| Bacteria: | |
| *Salmonella dublin* | Cattle |
| *Corynebacterium pseudoturberculosis* | Cattle |
| *Mycoplasma hyopneumoniae* | Swine |
| *Treponema hyodysenteriae* | Swine |
| *Brucella canis* | Dogs |
| Parasites: | |
| *Trichinella spiralis* | Swine |
| *Dicryocaulus filaria* | Sheep |
| *Dictyocaulus viviparous* | Cattle |
| *Dirofilaria imunitis* | Dogs |
| Fungi: | |
| *Trichophyton* spp. | Cattle, Horses |
| *Microsporum* spp. | Dogs, Cats |

Some common enzymes useful in carrying out the method of this invention are horseradish peroxidase, alkaline phosphatase, glucoamylase, carbonic anhydrase, acetylcholinesterase, glucose oxidase, urease and beta-galactosidase. Other enzymes, such as those listed in Table III of U.S. Pat. No. 4,275,149, column 22, lines 51–69 and column 23, lines 1–48 also apply.

A variety of substrates and chromophores are available for use with these enzymes. Horseradish peroxidase, for instance, employs $H_2O_2$ and one or more of the following example chromogens to generate a colored product: 5-amino salicylic acid, 2,2'-azino-bis (3-ethylbenzthiazoline-6-sulfamic acid), o-dianisidine, o-phenylenediamine and 3,3',5,5'-tetramethylbenzidine. Other examples for this and other enzymes are cited in U.S. Pat. No. 4,299,916, starting in column 29 in the section entitled "Chromophores and Fluorophore Reactions". Of particular interest are the peroxidases, which require a chromogenic substrate and an acceptor such as hydrogen peroxide or uric oxide, and the hydrolases, which require only a chromogenic substrate.

The invention is further illustrated by the following examples:

EXAMPLE 1

Preparation of Test Trays

Two milliliters (ml) of 95% ethanol were added to each of the four chambers of a Nunc tissue culture tray and allowed to incubate for ten minutes at room temperature. The ethanol was then decanted and the trays were allowed to dry. 2 ml of pseudorabies virus, Shope Strain PK15 (PRV), diluted in 0.1 M carbonate-bicarbonate buffer, pH 10.5, at a concentration of 40 µg protein per ml, are added to each well of the culture tray and incubated for three hours at room temperature. The excess antigen coating solution was discarded and 2.0 ml of a blocking agent, 1% non-fat milk in phosphate buffered saline, was added. After 20 minutes, the blocking solution was discarded and the wells of the tray are each immediately filled with 2.3 ml of 2% Type E agar in PBS at about 90° C. Covers are placed on the trays and when the agar had solidified, the trays were enclosed in foil pouches and sealed. The test trays were then stored under refrigerated conditions until needed.

EXAMPLE 2

Preparation of CAP

Rectangles, 61 mm×21 mm (with the four corners rounded) were cut from Schleicher and Schuel No. 410 paper. This size allows the product to lie flush on the, antigen coated plastic surface of the test tray and is such as to minimize slipping across the surface and provide a full background of white color against which the results of the final test are determined. After cutting out the paper rectangles and positioning them on a smooth flat surface, 1.8 ml of a hot chromogen-acceptor-agar solution (0.03% 3,3',5,5'-tetra-methylbenzidine, 0.006% hydrogen peroxide and 1.6% Sigma Type E agar) in 0.01 M PBS is applied to each rectangle. The temperature was maintained at about 75° C. during the preparation process. It is convenient to perform this process by having the paper in a tray of a similar design to the antigen coated trays. When the CAPs were prepared, a cover was placed on the storage tray and the CAPs were packaged in foil pouches to avoid air exposure. They were then transferred to a refrigerated environment until needed.

EXAMPLE 3

Addition of Sample

Samples of blood were collected in the field from the ears of a herd of swine to be tested for pseudorabies. The samples were collected on Schleicher and Schuell No. 903 paper, dried, identified, recorded, transported and stored until needed for testing. At the testing site, 0.25 inch diameter disks were punched from the sample treated paper and placed on the agar layer of a previously prepared test tray from Example 1.

EXAMPLE 4

Testing and Interpretation of Results

The sample disks of Example 3 in intimate contact with the agar layer were incubated on the surface of the agar for 2.5 hours at room temperature, to permit antibodies from the blood samples to migrate through the agar and bind to the antigen layer of the test tray. After the sample incubation, the agar slabs with the sample disk were removed by lifting one end of the agar and tilting the tray. Each chamber of the tray was washed once with about 3 ml of a solution of 0.1M Tris buffer, pH 7.0 containing 1% ovalbumin and 0.5% Tween 20. After a three minute incubation, the solution is discarded and each tray chamber is washed again with about 3 ml of 0.1M carbonate-bicarbonate buffer, pH 9.5. After three minutes, the second wash was then discarded and 2.0 ml of anti-pig IgG-peroxidase conjugate in Tris-Tween buffer was added to each chamber and incubated for one hour. After incubation with the conjugate, the excess solution was discarded and the surface was washed by the same procedure and with the same two wash solutions used after the sample incubation. CAPs previously prepared in Example 2 were added to each chamber and positioned to lie flat on the plastic surface. The tray was inverted and the color development noted after 15 minutes. The color was matched with known positive and negative reference samples and assignments of color level were recorded for each sample.

EXAMPLE 5

Application of System to BVD Virus

Bovine Viral Diarrhea (BVD), Shope Strain antigen, collected through a tissue culture technique similar to that for Pseudorabies (PRV) is prepared for coating by diluting it 80-fold in carbonate-bicarbonate buffer, pH 9.6. Some 2 ml of the diluted antigen, usually containing 5 to 50 micrograms of protein per ml, are added to each well of a Nunc four well tissue culture tray which has been pre-treated with alcohol as described for the PRV procedure. The antigen solution is incubated in tightly covered trays for three hours at 37° C. The liquid is then decanted and 2.0 ml of 1.0% nonfat milk in PBS are added to each well. After one hour incubation at room temperature, the solution is discarded and each well is filled with 2.3 ml of 2% Type E Agar as described for the PRV procedure. The trays are placed in a protective environment, such as a sealed foil bag, and stored at 4° C. until needed.

At the time of testing, 0.25 inch diameter paper disks (dry) impregnated with bovine blood or serum are placed on the surface of the agar. The samples are then allowed to incubate at room temperature for 2.5 hours. The agar and samples are then removed and the wells are washed as described earlier in the PRV procedure. After completion of the washing procedure, 2.0 ml of a 1:1400 dilution of rabbit anti-bovine IgG—horseradish peroxidase conjugate (Sigma Chemical Company, St. Louis, Mo.) in Tris-Tween buffer, pH 7.0 is added to each well. The Conjugate solution is allowed to incubate for one hour after which it is discarded and the wells are washed as described earlier for the PRV test. CAPs are then immediately positioned in the wells. The tray is inverted and color development is noted as described for tests with other antigens. Serum or blood samples containing BVD antibodies are detected by showing significant color development after approximately 15 minutes. Samples devoid of BVD antibodies have no or insignificant color development after 15 minutes from the time the CAPs were applied.

It is apparent that many modifications and variations of this invention as hereinbefore set forth may be made without departing from the spirit and scope thereof. The specific embodiments described are given by way of example only and the invention is limited only by the terms of the appended claims.

We claim:

1. A moist uniform non-laminar chromogen agar color reactive test sheet for use in ELISA diagnostic testing, which comprises a sheet of white absorbent material impregnated with a chromogen in the form of an enzyme substrate contained in solidified agar, said test sheet being sealed in foil or plastic to maintain its moisture.

2. A color reactive test sheet according to claim 1 wherein said chromogen is a substrate reactive with the enzyme of a species specific enzyme-linked anti-immunoglobulin.

3. A color reactive test sheet according to claim 1 wherein the test sheet includes an electron acceptor within said agar.

4. A color reactive test sheet according to claim 1 for use in a multicompartmented test tray wherein said test sheet is in the form of patches of a size and shape to fit the compartments of said tray.

* * * * *